(12) United States Patent
Wolf

(10) Patent No.: US 6,676,705 B1
(45) Date of Patent: Jan. 13, 2004

(54) VARIABLE TILT ANGLE TAPER LOCK SHOULDER PROSTHESIS

(76) Inventor: Eugene M. Wolf, 55 Montacito Rd., San Rafael, CA (US) 94901

( * ) Notice: Subject to any disclaimer, the term of this patent is extended or adjusted under 35 U.S.C. 154(b) by 162 days.

(21) Appl. No.: 09/953,582

(22) Filed: Sep. 13, 2001

(51) Int. Cl.$^7$ .................................................. A61F 2/40

(52) U.S. Cl. .................................................. 623/19.14

(58) Field of Search .................. 623/18.11, 19.11–19.14

(56) References Cited

U.S. PATENT DOCUMENTS

| | | |
|---|---|---|
| 3,694,820 A | 10/1972 | Scales et al. |
| 3,978,528 A | 9/1976 | Crep |
| 3,979,778 A | 9/1976 | Stroot |
| 4,042,980 A | 8/1977 | Swanson et al. |
| 4,045,826 A | 9/1977 | Stroot |
| 4,261,062 A | 4/1981 | Amstutz et al. |
| 4,279,041 A | 7/1981 | Buchholz |
| 4,378,607 A | 4/1983 | Wadsworth |
| 4,470,158 A | 9/1984 | Pappas et al. |
| 4,524,467 A * | 6/1985 | DeCarlo, Jr. .............. 623/19.12 |
| 4,550,450 A | 11/1985 | Kinnett |
| 4,773,417 A | 9/1988 | Moore et al. |
| 4,778,473 A | 10/1988 | Mathews et al. |
| 4,865,605 A * | 9/1989 | Dines et al. .............. 623/19.14 |
| 4,872,451 A | 10/1989 | Moore et al. |
| 4,901,717 A | 2/1990 | Moore et al. |
| 4,919,669 A * | 4/1990 | Lannelongue ............ 623/19.12 |
| 4,964,865 A | 10/1990 | Burkhead et al. |
| 4,973,211 A | 11/1990 | Potucek |
| 4,986,833 A | 1/1991 | Worland |
| 5,030,219 A | 7/1991 | Matsen, III et al. |
| 5,032,132 A | 7/1991 | Matsen, III et al. |
| 5,250,050 A | 10/1993 | Poggie et al. |

(List continued on next page.)

FOREIGN PATENT DOCUMENTS

| | | | |
|---|---|---|---|
| DE | 11 64 019 B | 2/1964 | |
| DE | 42 20 217 A1 | 12/1993 | .............. A61F/2/02 |
| EP | 0 375 582 A | 6/1990 | .............. A61F/2/38 |
| EP | 0 278 807 B1 | 4/1992 | .............. A61F/2/40 |
| EP | 0 460 886 B1 | 8/1997 | ........... A61B/17/15 |
| EP | 0 903 127 A2 | 3/1999 | .............. A61F/2/40 |
| EP | 0 940 126 A1 | 9/1999 | .............. A61F/2/40 |
| EP | 0 963 742 A1 | 12/1999 | .............. A61F/2/40 |
| FR | 2 418 644 | 9/1979 | .............. A61F/1/00 |
| FR | 2647670 | * 12/1990 | .............. A61F/2/40 |
| WO | WO 96/17553 | 6/1996 | ........... A61B/17/10 |
| WO | WO 97/10779 | 3/1997 | .............. A61F/2/40 |
| WO | WO 97/39693 | 10/1997 | ........... A61B/17/58 |
| WO | WO 98/18412 | 5/1998 | .............. A61F/2/36 |
| WO | WO 98/46172 | 10/1998 | .............. A61F/2/40 |
| WO | WO 99/44546 | 9/1999 | .............. A61F/2/40 |

OTHER PUBLICATIONS

Cooper, R.A., et al., "Recurrent Disassembly of a Modular Humeral Prosthesis," *The Journal of Arthroplasy*, vol. 6, No. 4, Dec. 1991, pp. 375–377.

(List continued on next page.)

*Primary Examiner*—Kevin Shaver
*Assistant Examiner*—Michael B. Priddy
(74) *Attorney, Agent, or Firm*—Gray Cary Ware & Friedenrich, LLP; Andrew V. Smith

(57) ABSTRACT

A variable tilt angle shoulder prosthesis includes a variable tilt angle, comprising a head component including a proximal portion configured to interface with a glenoid process and a distal surface including a socket depression defined therein; a humeral shaft; a humeral neck at the end of the shaft including a proximal ball end which is configured to couple with the socket depression of the humeral head as a ball-in socket joint, adjustable, upon coupling with said humeral neck, to a selected tilt angle among a plurality of tilt angles relative to an elongate direction of said shaft to substantially match said prosthesis to a natural tilt angle of a humeral head of a patient.

21 Claims, 5 Drawing Sheets

U.S. PATENT DOCUMENTS

| | | |
|---|---|---|
| 5,271,737 A | 12/1993 | Baldwin et al. |
| 5,282,865 A | 2/1994 | Dong |
| 5,314,479 A | 5/1994 | Rockwood, Jr. et al. |
| 5,326,366 A | 7/1994 | Pascarella et al. |
| 5,330,531 A | 7/1994 | Capanna |
| 5,403,320 A | 4/1995 | Luman et al. |
| 5,489,309 A | 2/1996 | Lackey et al. |
| 5,507,817 A | 4/1996 | Craig et al. |
| 5,507,819 A * | 4/1996 | Wolf ........................ 623/19.11 |
| 5,571,203 A | 11/1996 | Masini |
| 5,597,383 A | 1/1997 | Carbone |
| 5,601,562 A | 2/1997 | Wolf et al. .................... 606/86 |
| 5,658,350 A | 8/1997 | Carbone ........................ 623/23 |
| 5,665,090 A | 9/1997 | Rockwood et al. ............ 606/80 |
| 5,702,486 A | 12/1997 | Craig et al. .................... 623/23 |
| 5,728,161 A | 3/1998 | Camino et al. ................ 623/19 |
| 5,775,334 A | 7/1998 | Lamb et al. ................. 128/845 |
| 5,779,710 A | 7/1998 | Matsen, III .................. 606/102 |
| 5,800,551 A | 9/1998 | Williamson et al. ........... 623/19 |
| 5,888,203 A | 3/1999 | Goldberg ...................... 623/21 |
| 5,895,425 A | 4/1999 | Grafton et al. ................ 623/16 |
| 5,906,644 A | 5/1999 | Powell .......................... 623/23 |
| 5,957,979 A | 9/1999 | Beckman et al. .............. 623/20 |
| 6,197,062 B1 | 3/2001 | Fenlin ...................... 623/19.12 |
| 6,197,063 B1 | 3/2001 | Dews ....................... 623/19.14 |
| 6,214,053 B1 * | 4/2001 | Ling et al. ................ 623/23.11 |
| 2001/0047210 A1 | 11/2001 | Wolf ........................ 623/19.14 |

OTHER PUBLICATIONS

Pearl et al., "Retroversion of the Proximal Humerus in Relationship to Prosthetic Replacement Arthroplasty," *J. Shoulder Elbow Surg.*, 1995 vol. 4, No. 4, pp. 286–289.

Mallon et al., "Radiographic and Geometric Anatomy of the Scapula," *Radiographic Scapular Anatomy*, Apr. 1992, No. 277, pp. 142–154.

Boileau, et al., "Journal of Shoulder and Elbow Surgery," Jan./Feb. 1993, S12 Abstracts.

Blevins, F.T., et al., "Dissociation of Modular Humeral Head Components: A Biomechanical and Implant Retrieval Study," *J. Shoulder Elbow Surg.*, Mar./Apr. 1997, pp. 113–124.

Torchia, M.E., et al., "Total Shoulder Arthroplasty with the Neer Prosthesis: Long–term Results," *J. Shoulder Elbow Surg.*, Nov./Dec. 1997, pp. 495–505.

Fenlin, J.M., Jr., et al., "Indications, Technique, and Results of Total Shoulder Arthroplasty in Osteoarthritis," *Total Shoulder Arthroplasty: Orthopedic Clinics of America*, vol. 29, No. 3, Jul. 1998, pp. 423–434.

Cuomo, F., et al., "Avoiding Pitfalls and Complications in Total Shoulder Arthroplasty," *Total Shoulder Arthroplasty: Orthopedic Clinics of America*, vol. 29, No. 3, Jul. 1998, pp. 507–518.

Cameron, B., et al., "Periprosthetic Fractures of the Humerus and Scapula," *Total Shoulder Arthroplasty:Orthopaedic Clinics of America*, vol. 30, No. 2, Apr. 1999, pp. 305–318.

Walch, G., et al., "Prosthetic Adaptability: A New Concept for Shoulder Arthroplasty," *J. Shoulder Elbow Surg.*, Sep./Oct. 1999, pp. 443–451.

Brown, T.D., et al., "Complications with Humeral Head Replacement," *Total Shoulder Arthroplasty:Orthopedic Clinics of America*, vol. 31, No. 1, Jan. 2000, pp. 77–90.

O Levy, et al., "Cementless Surface Replacement Arthroplasty of the Shoulder," *The Journal of Bone and Joint Surgery*, vol. 83–B, No. 23, Mar. 2001, pp. 213–221.

Copeland Shoulder—Report produced by Biomet & Merck.

* cited by examiner

VARIABLE TILT ANGLE TAPER LOCK SHOULDER PROSTHESIS

BACKGROUND OF THE INVENTION

1. Field of Invention

This invention relates generally to a a variable tilt angle shoulder prosthesis comprising a head component having a socket depression that will mate with a proximal hemispherical dome end of the humeral neck as a ball-in socket joint, such that said head is capable of rotating along any circumference of the proximal ball end end of the humeral neck imitate the natural radial tilt angle of a patient's humerus.

2. Description of the Related Art

The French surgeon Paean is considered to be the first surgeon to perform a shoulder replacement, when he implanted a rubber and platinum prosthesis in the shoulder of a 37-year-old baker with tuberculous arthritis in 1893. Paean was also credited with the first complication and revision when he removed the prosthesis 2 years later because of recurrent infection. In 1951, Neer introduced hemiarthroplasty as a treatment option for proximal humerus fractures and fracture dislocations. He soon expanded his indications to the treatment of glenohumeral arthritis. Cameron, B, 30(2) ORTHOP CLIN NORTH AM 305–309, 305–6 (1999). In 1974, Neer described the pathologic findings of glenohumeral arthritis and reported successful treatment with shoulder arthroplasty. In 1982, he reported on a series of patients with osteoarthritis treated successfully with total shoulder arthroplasty. Since then, shoulder arthroplasty has become the standard treatment for advanced osteoarthritis of the glenohumeral joint (Fenlin, J M and Frieman, 29(3) ORTHOP CLIN NORTH AM 423–34, 423 (1998)).

Constrained shoulder arthroplasty became popular in the 1970s to restore the stability that was presumably lost in the setting of rotator cuff insufficiency. These implants have largely been abandoned because of their limited success and high complication rate, including prosthetic and periprosthetic fracture of both the glenoid and the humerus. Neer performed his last fixed fulcrum arthroplasty in 1973, when he redesigned the humeral component so that it could articulate with a polyethylene glenoid component that conformed to the contour of the glenoid articular surface. (Cameron, Id., at 305–6.).

The indications for hemiarthroplasty broadened to include primary osteoarthritis, rheumatoid arthritis, rotator cuff arthropathy, and avascular necrosis. This technique offered surgeons a broader range of treatment options and heralded the resurgence of a new interest in the field. (Brown, T and Bigliani, L, 31(1) ORTHOP CLIN NORTH AM 77–90, 77 (2000)).

Most current implant systems are a variation of Neer's original design. Cameron, B, 30(2) ORTHOP CLIN NORTH AM 305–309, 305–6 (1999). The primary indication for total shoulder arthroplasty in osteoarthritis of the glenohumeral joint is severe, chronic, and progressive shoulder pain. Usually the pain is accompanied by decreased range of motion and compromised function. Surgery may be considered when symptoms become refractory to conservative treatment such as anti-inflammatory medication, rest, and physical therapy (Fenlin, J M and Frieman, 29(3) ORTHOP CLIN NORTH AM 423–34, 423 (1998)).

The human shoulder varies amongst patients in two important aspects: the tilt angle between the distal humerus and the proximal neck; and the radial offset. The radial offset is the rotation of the humeral head itself along the radius of the neck, and may be in any direction. Poorly fitting devices can result in complications including aseptic loosening, periprosthetic fracture, and anterior or posterior instability.

Humeral radial offset is related to subscapularis function and integrity. It has been recommended that re-establishment of the lateral humeral offset (the distance from the base of the coracoid process to the lateral-most point of the greater tuberosity) close to the anatomical position is important for biomechanical function. Overstuffing the joint with a thick metal-backed glenoid component or an excessively large humeral head implant may dramatically increase the lateral humeral offset, creating an internal rotation contracture and placing excessive stress on the subscapularis repair. (Cuomo, F., and Checroun, A., 29(3) ORTHOP CLIN NORTH AM 507–18, AT 08–09 (1998)).

Artifact often makes visualization of soft tissue structures by magnetic resonance imaging suboptimal; however, it may occasionally enable the surgeon to assess the integrity of the rotator cuff tendon. This assessment is important, particularly when planning preoperatively for massive tears that might require tendon transfers or use of a tendon allograft. Computed tomography (CT) scans require special techniques to minimize artifact from the component but may be useful for evaluating bone stock, tuberosity fracture healing, or glenoid version and wear. If a rotator cuff tear is suspected, a routine arthrogram can prove to be invaluable for diagnosing full-thickness tears. Arthroscopy in this patient population may prove beneficial, although its indications for diagnosis and treatment require better definition. (Brown, T. and Bigliani, L, 31 (1) ORTHOP CLIN NORTH AM 77–90, 78–9 (2000)).

To insert a prosthetic device, the humeral medullary canal is reamed or broached (depending on the prosthetic design) by hand or power until minimal resistance is met. This is more of a sizing procedure than a reaming procedure. Most of the patients who undergo prosthetic replacement for osteoarthritis are also osteopenic, and it is very easy to split the proximal humerus by overzealous reaming or broaching.

Prostheses may be cemented into place, or press-fitted. Fenlin's preference is to use cement in all cases of osteoarthritis, with the exception of younger individuals with excellent bone quality, because the majority of cases with humeral side loosening are in uncemented cases. (Fenlin, J M and Frieman, 29(3) ORTHOP CLIN NORTH AM 423–34, 428 (1998)). Torchia reports that a shift in position of the humeral component occurred in 49% of the press-fit stems and none of the cemented stems in a series of 113 shoulder replacements between 1975 and 1981. (Torchia, M E, Cofield, R H, Settergren, C R, 6(6) J SHOULDER ELBOW SURG 495–505 (1997)).

Shoulder replacement continues to share many of the numerous complications encountered with other major joint replacements, including instability, aseptic loosening, infection, periprosthetic fracture, deltoid dysfunction, rotator cuff tears, modular implant dissociation, neural injury, and heterotopic ossification. The incidence of such complications can be minimized by the surgeon's use of appropriate surgical indications, precise surgical and sterile technique, attention to detail, a tailored rehabilitation program, and a thorough understanding of shoulder anatomy and kinematics. (Brown, T and Bigliani, L, 31(1) ORTHOP CLIN NORTH AM 77–90, 77 (2000)).

Precise soft tissue balancing and proper prosthetic positioning are needed to restore both rotational and translational components of normal shoulder kinematics. Soft tissues must be perfectly balanced, symptomatic subluxation or dislocation may result. Posterior, anterior, and inferior stability must be evaluated and accurately determined during each procedure. With the trial components in place, stability is tested by employing several specific maneuvers. Posterior stability is assessed with the posterior drawer test and with flexion of the internally rotated arm. This arm position is required for many important activities of daily living. Anterior stability may be tested with an anterior drawer and by external rotation with the arm abducted and at the side. Inferior stability is evaluated by downward traction on the arm in neutral rotation. (Id., at 509.).

Complications associated with humeral head replacement have been of concern since the first shoulder arthroplasty was performed by Paean in 1893. Although this patient did reasonably well for 2 years, a resection arthroplasty was ultimately required because of a postoperative course complicated by a chronic infection of the prosthesis. Subsequently, this method of treatment for glenohumeral dysfunction was largely abandoned until 60 years later, when Neer introduced the humeral prosthesis in the early 1950s. (Brown, T, and Bigliani, L, supra, at 77.).

A 1988 review by Fenlin and Frieman reported varying degrees of success amongst clinical teams. Matsen's early outcome data showed that patients with arthritis of the glenohumeral joint treated with nonconstrained total shoulder arthroplasty demonstrated substantial and statistically valid improvements in pain, function, and general health that occurred within 6 months of surgery and remained stable in short-term follow-up. In 1998, Cofield reported rates of loosening with cementless techniques. Review of the literature for cemented humeral stems over more than a decade reveals a 0% revision rate and a 6% rate of radiolucent lines. Uncemented press-fitted humeral components from 11 published studies had less than 1% loosening. Torchia and Cofield have reported lucencies around the uncemented humeral stem approaching 50% in long-term follow-up using the Neer II prosthesis. (Fenlin, J M and Frieman, 29(3) ORTHOP CLIN NORTH AM 423–34, 432–3 (1998) [Internal Citations Omitted]).

Currently, nonconstrained total shoulder arthroplasty is the treatment of choice for patients with osteoarthritis of the glenohumeral joint. This procedure is technically precise, and when performed properly in selected patients, can be expected to provide reliable pain relief and improvement in function in greater than 90% of patients, with greater than 90% survival rate at 5 years. (Fenlin, J, and Frieman, B, 29(3) ORTHOP CLIN NORTH AM 423–34, 434(1998)). The current clinical success of shoulder replacement surgery has essentially paralleled the experience of major joint replacement of the hip and knee for osteoarthritis. Many authors have demonstrated consistent relief of pain as well as significant improvement of function in more than 90% of shoulders.

Despite encouraging results, authors report short-term and long-term complications, which adversely affect the clinical course in 12% to 16% of shoulder replacements. In order of decreasing frequency, the major complications associated with unconstrained implants include glenoid loosening, instability, tearing of the rotator cuff, periprosthetic fracture, and infection. With the advent of glenoid resurfacing in the 1970s, the incidence of periprosthetic fracture of the humerus and glenoid has risen to its current rate of 1% to 3%. This trend is probably related to attempts to gain access to the glenoid (Cameron, B, 30(2) ORTHOP CLIN NORTH AM 305–309 (1999)).

Fractures of the humerus and scapula may occur during surgery as well as in the postoperative period. No cases of periprosthetic fracture are reported among Neer's initial series. However, the overall prevalence of periprosthetic fractures varies between 0.5% and 3%, constituting about 20% of all complications associated with shoulder arthroplasty. These are primarily humeral shaft fractures, the majority occurring intraoperatively. Postoperatively, humeral shaft fractures also occur with greatest frequency. Cameron, supra, at 306. These fractures predominantly involve the humeral shaft and may occur less commonly at the glenoid, coracoid, or acromion. The presence of a prosthesis, in association with a humeral shaft fracture, confers a higher nonunion rate than that of a humeral shaft fracture alone, regardless of the method of treatment. Altered mechanical factors, in association with various host factors such as age, osteopenia, and medical condition, may delay or inhibit healing. Some mechanisms of injury are unique to intraoperative periprosthetic fractures, but three risk factors—age, osteopenia, and rheumatoid arthritis—are shared by the intraoperative and postoperative groups. Treatment decisions should be guided by the ultimate objectives of fracture union, in concert with the maintenance of glenohumeral motion and restoration of function. Major residual impairment is often present after union when the latter two objectives cannot be fulfilled, reinforcing the importance of both prevention of such fractures and proper management of the fractures when they occur. (Cameron, B., 30(2) ORTHOP CLIN NORTH AM 305–309, 305 (1999), INCIDENCE).

Accommodating for improper positioning by excessive levering of the distal humerus or excessive forceful external rotation predisposes to fracture of the humeral shaft. In addition, difficult exposure, osteoporosis, or overreaming of the medullary canal may result in cortical perforation. Cameron, supra, at 307. Use of a large initial broach, failure to ream sequentially, and overly aggressive reaming may primarily fracture the humerus. Moreover, if the distal canal has been incompletely broached, the tip of the prosthesis may create a wedge effect on final impaction, leading to fracture at the tip of the stem. Overzealous reaming creates a stress riser as a result of endosteal notching. (Cameron, supra, At 308).

Close scrutiny of prefracture radiographs occasionally reveals evidence of premorbid stress risers, such as endosteal notching, cortical perforation, stem penetration, and varus alignment of the humeral component with abutment of the stem against the lateral cortex. Some fractures may be prevented by preoperative templating, combined with careful manipulation of the arm, and proper broaching and reaming techniques. A loose humeral implant has been associated with subsequent fracture, but no clear causal relationship has been established in the shoulder literature as it has for the hip. Cameron, supra at 309.

In addition to fracture, various types of stability may result from an improperly positioned device. Anterior instability is most often attributed to subscapularis tendon rupture, malrotation (relative anteversion) of the humeral prosthesis, and anterior deltoid dysfunction. Brown, T and Bigliani, L, 31(1) ORTHOP CLIN NORTH AM 77–90, 78–9 (2000). Posterior instability after hemiarthroplasty results most commonly from malposition of the prosthesis, soft tissue imbalances, or both. The use of a hemiarthroplasty in a patient with longstanding osteoarthritis or excessive glenoid retroversion may also lead to posterior subluxation or dislocation if posterior glenoid wear is not recognized and appropriately addressed. The surgeon should have a high index of suspicion with patients relating a history of multiple glenohumeral dislocations or demonstrating markedly limited external rotation clinically. Thorough preoperative planning to assess the glenoid for the presence of excessive posterior wear can minimize the risk of this complication. This planning is best accomplished by obtaining an axillary lateral radiograph with a contralateral view for comparison. If adequate visualization of the posterior glenoid rim is not possible, preoperative CT is indicated. (Brown, T and Bigliani, L, at 81).

The propensity of the uncemented component for loosening relative to cemented humeral prosthesis has been discussed in several studies. Sneppen et al reviewed a series of 62-Neer total shoulder arthroplasties with an average follow-up of 92 months (range, 52 to 139 months). Of the 50 cemented components, only 1 showed incomplete lucency. In the 12 press-fit humeral components, 5 showed progressive loosening, 4 of which were noted to have associated subsidence. Although the uncemented prosthesis had a higher rate of radiographic loosening, they were rarely symptomatic clinically. Torchia and Cofield reported that 41 of 81 press-fit humeral components demonstrated loosening at a mean radiographic follow-up of 9.7 years (range, 5 to 17 years). None of the nine cemented components showed any signs of loosening at a minimum of 5 years. (Brown, T., and Bigliani, 31(1) ORTHOP CLIN NORTH AM 77–90, 82 (2000).

Improper placement can result in eccentric reaming of the humeral canal and subsequent perforation of the humeral shaft. The entry point should enter superolaterally in an eccentric position just posterior to the bicipital groove. While reaming the shaft, attention must be paid to directing the reamers longitudinally down the medullary canal and avoiding perforation of the canal. (Brown T and Bigliani L, 31(1) ORTHOP CLIN NORTH AM 77–90, 83 (2000)).

In efforts to reduce the occurrence of these adverse experiences, orthopedists have used various types of shoulder prostheses. One problem with conventional unitary shoulder prostheses was the necessity of maintaining large inventories of differently configured prostheses to accommodate patients' differing anatomies. Not only were prostheses with different sizes of heads and stems required, but also prostheses with the head and stem configured at various tilt angles and radial offsets relative to one another. These various configurations were required in each size category.

To reduce the required inventory, assorted modular prostheses have been devised. Prior art modular systems have generally been designed to allow flexibility with respect to either the tilt angle or the radial offset between the head and stem. Modular humeral head components were introduced in the 1980s in an effort to provide flexibility with soft tissue balancing, maximize the fit of the proximal humerus, reproduce the body's normal anatomy, and facilitate future revisions. The modular components have successfully achieved many of these goals; however, they have also spawned a new set of problems unique to their design. Modularity of the humeral component is achieved through a conical press-fit (Morse taper) involving a tapered shank that fits into a socket of the corresponding taper. (Brown, T and Bigliani, L, 31 (1) ORTHOP CLIN NORTH AM 7790 84–5 (2000)). Modularity can offer the surgeon more flexibility to reconstruct the glenohumeral joint anatomically, theoretically decreasing complications such as instability.

Early reports using a modular prosthesis were encouraging, but long-term studies are still lacking (Fenlin, J, and Frieman, B, 29(3) ORTHOP CLIN NORTH AM 423–34, 433 (1998)). The addition of modularity may play a role in decreasing the incidence of periprosthetic fractures, especially in the revision setting. Cameron, supra, at 306. Although some of these prior art modular systems utilize either a "standard" head or a "standard" stem, most still require a plurality of either the heads or the stems to provide complete tilt angle and radial offset flexibility. None of the prior art systems provides complete tilt angle and radial offset flexibility without requiring different modular head or stem components of each given size. As a result, substantial inventories of either the stems or heads, which are the most expensive components, have had to be maintained. For instance, Walch, B., and Boileau, P., report a cemented prosthesis made in 3 different stem sizes, 7 humeral head sizes and a variable humeral neck compnent. Four different Humeral necks are available at four tilt angles, 125 degrees, 130 degrees, 135 degrees and 140 degrees and an eccentric dial located on the undersurface of the head permits eight different possible positions with which to reproduce the offset of the head. (Walch, G., and Boileau, P., 8(5) SHOULDER ELBOW SURG 443–51 (1999)). Use of this system resulted in an 8% complication rate leading to six revisions (6%). (Id).

Modular systems require the use of multiple sizes of several different modules that could be used in a "mix and match" manner to find the best fit for a particular patient. However, all of these modules rely on connecting pieces between the humeral head and the distal shaft to adjust the critical femoral tilt and radial offset. Duplicating a patient's radial offset, even more than the femoral tilt, has posed a difficult problem that has not been adequately solved to this date. In all of the modular prostheses currently in use, the humeral head may only be attached such that its planar surface remains perpendicular to the most proximal module.

Examples of modular prostheses include U.S. Pat. No. 6,197,062, to Fenlin, that describes a shoulder prosthesis system including a plurality of connectors for interconnecting "standard" shoulder prosthesis stems with "standard" shoulder prosthesis heads. The connectors enable a selected stem to be interconnected with a selected head in a plurality of configurations having various tilt angles, and radial offsets and lengths (See FIG. 4, Fenlin's FIGS. 8 and 9).

U.S. Pat. No. 6,197,063, to Dews, describes a modular system with two connectors between the head and the humeral shaft, the distal connector being capable of rotating 360° about the axis of the humeral shaft, and the proximal connector being capable of rotating 360° about the axis of the distal connector. The axes of the two connectors may be set as offset from each other in order to cause the first connector to be offset from the second connector, imitating the radial offset of the humeral head. See FIG. 5, Dews FIGS. 1 and 2. The first and second engagement means each comprise a male portion, and the head and stem are provided with corresponding mating female portions. Both Fenlin and Dews may utilize a Morse taper between the head and proximal stem, wherein the male and female portions preferably each have a substantially circular cross-sections, and a substantially self-locking tapered configuration (See FIG. 1).

U.S. Pat. No. 5,489,309, to Lackey, et. al. describes a prosthesis that features a head which lies in the glenoid cavity, a body that is placed in the proximal end of the humerus, and a primary and secondary stem which fits in the humeral canal. The head attaches to a platform on the proximal end of the body and the primary stem attaches to the distal end of the body with a male/female locking mechanism. The secondary stem attaches to the primary stem with male/female locking mechanism, and may be anti-rotational.

Theoretical disadvantages associated with the use of modular humeral components include corrosion and fretting at the head-stem interface and prosthesis dissociation. A few cases of humeral head dissociation have been noted with a modular humeral component. Cooper and Brems described a patient with recurrent dissociations of a modular humeral head component. The patient did not relate any history of trauma and was unable to determine exactly when the component became disassembled. (Cooper R, and Brems J, 6 J ARTHROPLASTY 375–377 (1991)). These findings were further supported by the series of Blevins et al of 13 dissociations of the same modular humeral head component. (Blevins F, Deng X, Torzilli P, et al, 6 J SHOULDER ELBOW SURG 113–124 (1997)). All but one of the dissociations occurred within 6 weeks of surgery, and none of the incidents was associated with trauma or dislocation of the implant. The authors attributed the dissociations largely to the reverse taper present on that particular prosthesis. (Cited in Brown, T and Bigliani, L, 31(1) ORTHOP CLIN NORTH AM 77–90 84–5 (2000)).

The risk of such complications can be minimized with proper surgical technique. This technique requires visualization of the entire proximal humeral base. The surgical field should be free of excess soft tissue, and all bony encroachments should be removed. With the trial components in place, the presence of impingement of the head on the greater tuberosity or abnormal laxity should be recognized and addressed. The components should be thoroughly dried with meticulous attention directed to the Morse taper articulation. Of theoretical concern is the use of a press-fit technique in conjunction with a collarless component, which could allow the modular head to subside onto the bony calcar and disengage. (Brown, T and Bigliani, L, 31(1) ORTHOP CLIN NORTH AM 77–90, 85 (2000)).

FIG. 4 shows the modular system of U.S. Pat. No. 6,197,062 to Fenlin, utilizing a plurality of connectors to enable a selected stem to be interconnected with a selected head in a plurality of configurations having various tilt angles, and radial offsets and lengths.

FIG. 5 shows the modular system of U.S. Pat. No. 6,197,063 to Dews, requiring two connectors that may be set as offset from each other in order to cause the first connector to be offset from the second connector to imitate the radial offset of the humeral head.

SUMMARY OF INVENTION

The present invention provides for a shoulder prosthesis in only two modules that permits the surgeon to precisely adjust the radial offset to fit the patient's own humerus by utilizing a head component including a proximal portion configured to interface with a glenoid process and a distal surface including a socket depression defined therein; a humeral shaft; a humeral neck at the end of the shaft including a proximal ball end which overhangs from a circumference of the humeral neck and which is configured to couple with the socket depression of the humeral head as a ball-in socket joint; and wherein said humeral head is adjustable, upon coupling with said humeral neck, to a selected tilt angle among a plurality of tilt angles relative to an elongate direction of said shaft to substantially match said prosthesis to a natural tilt angle of a humeral head of a patient.

In another embodiment, the humeral head is set position among a plurality of positions lattitudinally relative to said proximal ball end for substantially matching said prosthesis to a natural tilt angle of a humeral head of a patient.

In yet another embodiment of the invention, the humeral head is configured to be rotated, after being mated with said humeral neck, in a latitudinal direction relative to said proximal ball end of said neck to a set position for substantially matching said prosthesis to a natural tilt angle of a humeral head of a patient. Both the socket depression of the head component and the proximal ball end may be, but are not necessarily, hemishperical; and the distal surface of the head component may be, but is not necessarily, planar. The proximal ball end may, but does not necessarily have an overhang that extends from the circumference of the humeral neck, which may optionally contain a fin extending superiorly from the angled portion of the humeral neck.

The humeral shaft and neck, and head component, may be made of materials well known to those of ordinary skill in the art, including metal, polyethylene, and plastic. In a preferred embodiment, the humeral neck further comprises a fin extending superiorly from the angled portion, said fin containing depressions of a lattice-like structure for stability. The humeral shaft and neck may be made available at different shaft and neck lengths, and different tilt angles between the shaft and the neck.

The invention also describes a method of replacing a humeral head of a patient with a variable tilt angle prosthesis, comprising the steps of (a) resecting a proximal end of a humerus of the patient to remove the head and expose a medullary canal of the humerus; (b) inserting a stem of a prosthesis, said prosthesis including a shaft, a neck and a head adapted to approximate a dimension of said humeral head of said patient, into the medullary canal of the resected humerus; said prosthesis comprising a head component having a proximal portion configured to interface with a glenoid process and a distal surface including a socket depression defined therein; a humeral shaft; and a humeral neck at the end of the shaft including a proximal ball end which overhangs from a circumference of the humeral neck and which is configured to couple with the socket depression of the humeral head as a ball-in socket joint; and wherein said humeral head is adjustable, upon coupling with said humeral neck, to a selected tilt angle among a plurality of tilt angles relative to an elongate direction of said shaft to substantially match said prosthesis to a natural tilt angle of a humeral head of a patient. The prosthesis is set upon coupling with said humeral neck, to a selected tilt angle among a plurality of tilt angles relative to an elongate direction of said shaft to substantially match said prosthesis to a natural tilt angle of a humeral head of a patient.

The method may be practiced by setting, adjusting, or rotaing the head component at a position among a plurality of positions lattitudinally relative to said proximal ball end of said humeral neck to substantially match a natural tilt angle of a humeral head of a patient. This embodiment may be perfomed by the steps of (i) observing a first position for the socket depression of the humeral head at the apex of the proximal ball end of said humeral neck; (ii) selecting a second position from among a plurality of points along a lattitude of the proximal ball end of the humeral neck located at about 30 degrees from the apex of said proximal ball end; (iii) adjusting the lattitudinal position of the apex of the socket depression relative to the apex of the proximal ball end of the humeral neck along the longitude between the first and second position.

The humeral head of may advantageously further comprise the step of securing the humeral head at the patient's natural radial tilt angle.

BRIEF DESCRIPTION OF THE DRAWINGS

The invention will now be described, by way of example, with reference to the accompanying drawings, in which.

Figure 3:
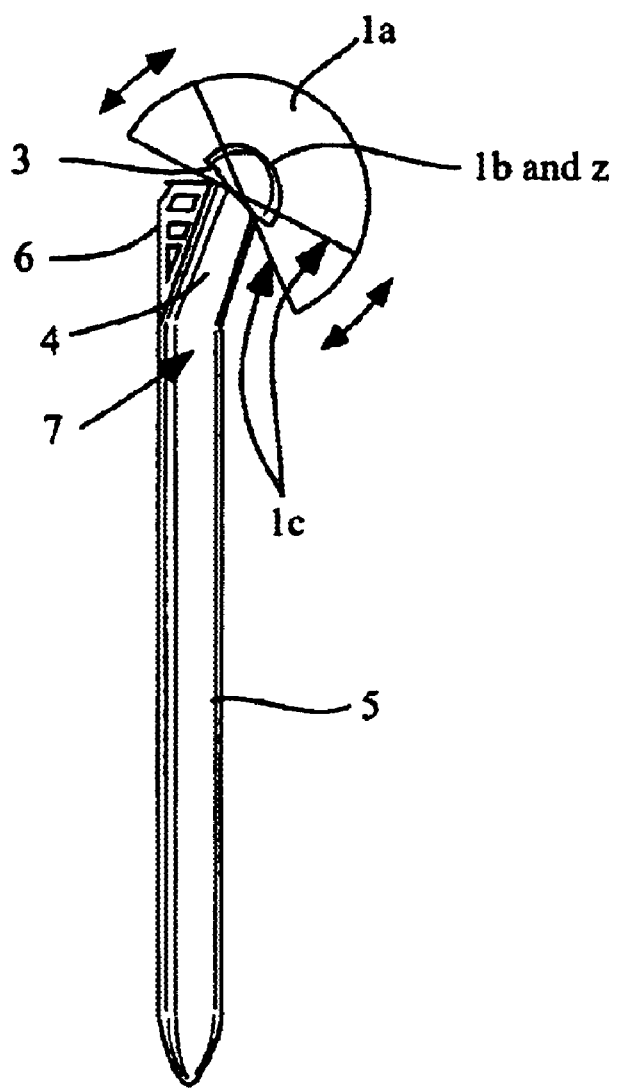

1a: humeral head;
1b: socket depression in distal humeral head;
1c: planar surface of the humeral head;
2: proximal ball end end of humeral neck;
3: overhang of proximal ball end end extending beyond radius of humeral neck;
4: humeral neck;
5: humeral shaft;
6: fin;
7: tilt angle between humeral shaft and neck;

FIG. 3 is an anterior view of an embodiment of the invention showing the humeral head in contact with the proximal ball end end of the humeral neck (1b and 2).

Figure 4:
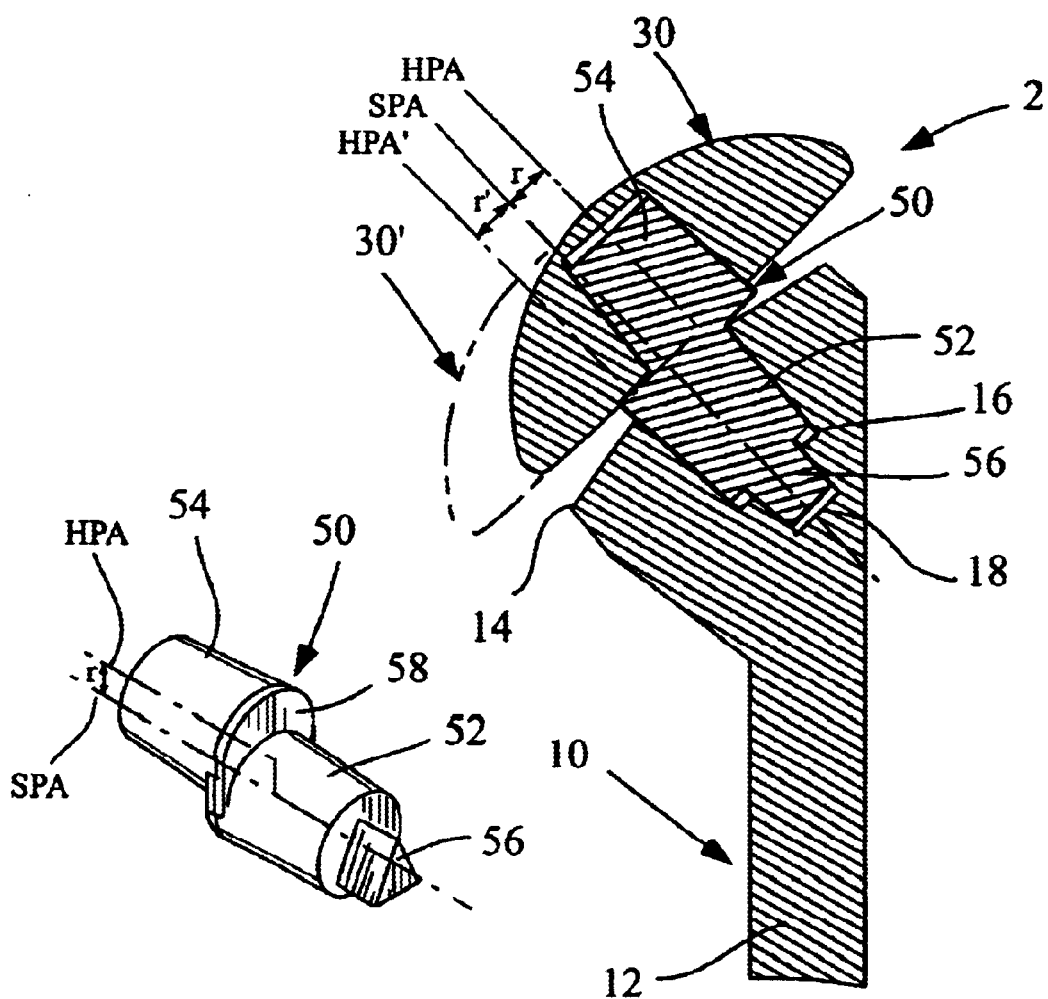

FIG. 4 shows the modular system of U.S. Pat. No. 6,197,062 to Fenlin, utilizing a plurality of connectors to enable a selected stem to be interconnected with a selected head in a plurality of configurations having various tilt angles, and radial offsets and lengths.

Figure 5:
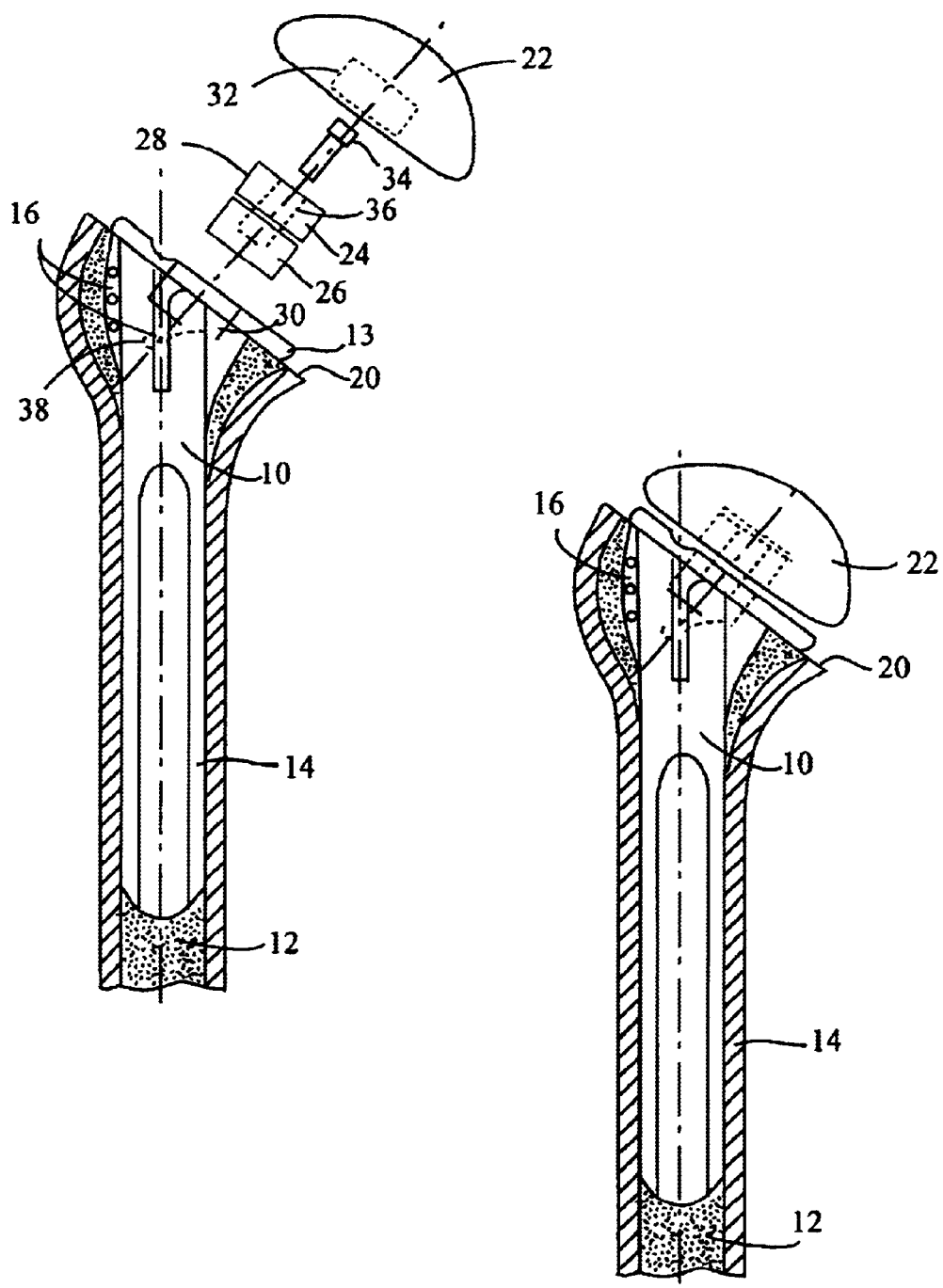

FIG. 5 shows the modular system of U.S. Pat. No. 6,197,063 to Dews, requiring two connectors that may be set as offset from each other in order to cause the first connector to be offset from the second connector to imitate the radial offset of the humeral head.

DETAILED DESCRIPTION OF THE PREFERRED EMBODIMENT

The following discussion of the preferred embodiment of the present invention is merely exemplary in nature and is in no way intended to limit the invention or its application or uses.

Figure 1:
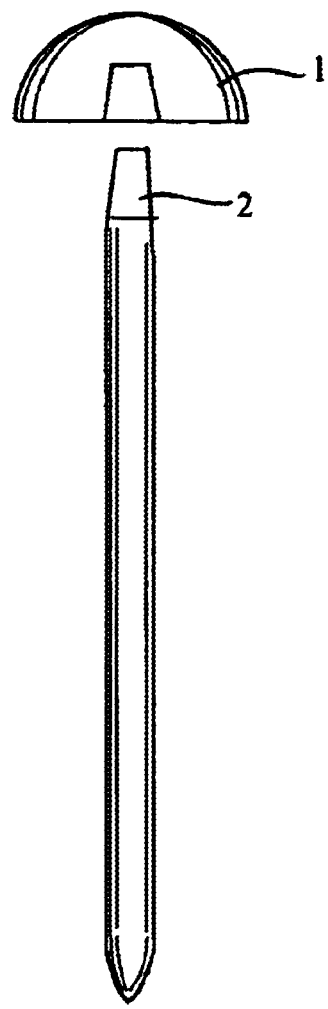
FIG. 1 is diagram of the conical head depression (1) and conical proximal humeral end (2) in use in most modular systems.
Figure 2:
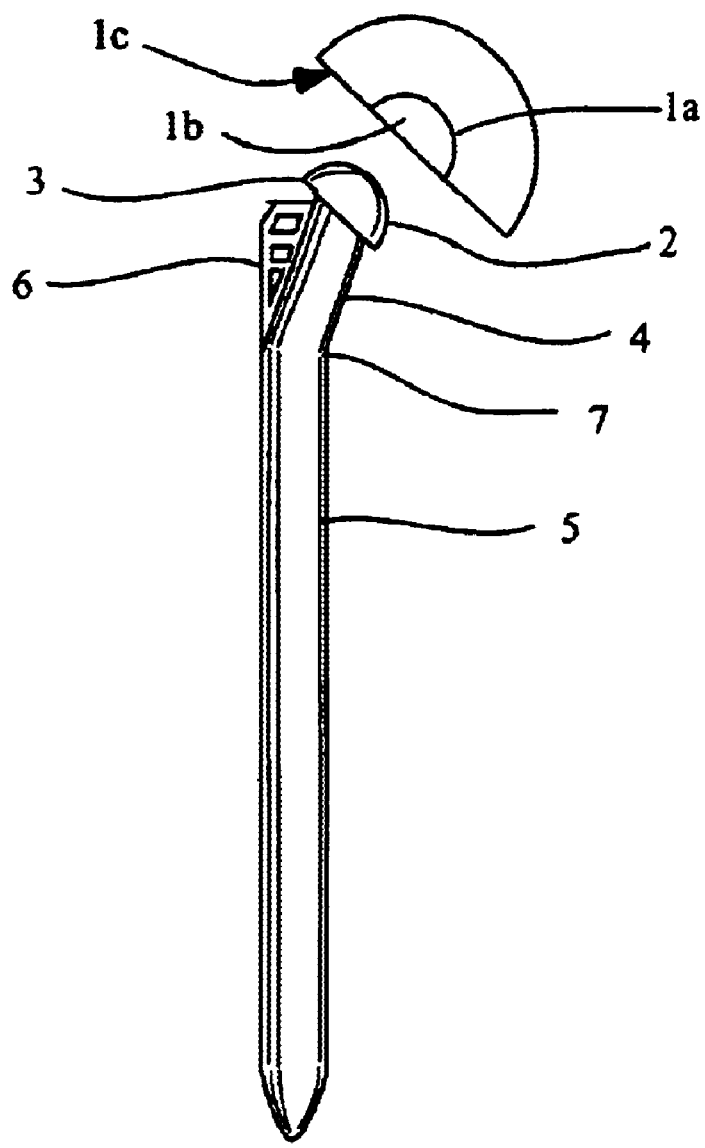
FIG. 2 is an anterior view of one embodiment of a humeral prosthesis according to the invention. In this Figure, the humeral head is detached from the humeral neck to reveal the following features.

Referring now to FIG. 2, a variable tilt angle shoulder prosthesis according to a preferred embodiment of the present invention is shown. The variable tilt shoulder prosthesis is used to replace a natural shoulder after the natural shoulder has degenerated. The variable tilt shoulder prosthesis includes a humeral head 1a having a socket depression 1b in the distal humeral planar surface 1c of the humeral head 1a; a proximal ball end 2 of humeral neck 4 having an overhang 3 of proximal ball end 2 extending, e.g., from less than a centimeter up to several centimeters, beyond circumference of humeral neck 4; and a humeral shaft 5. In a preferred embodiment, the variable tilt shoulder prosthesis further comprises a fin 6. In a more preferred embodiment, the prosthesis is available at various tilt angles 7 and with the humeral neck 4 and shaft 5 at a selected one of various sizes, so that the prosthesis may be configured to fit the particular anatomy of the patient.

As used herein, the unitary humeral neck 4 and shaft 5 will be used to represent one of a plurality of humeral neck 4 and shaft 5 components which are similar to that which is shown in FIG. 2 but which are of different sizes and different tilt angles 7. Similarly, the humeral head 1 will also be used to represent one of a plurality of similar components that are of different sizes. The proximal ball end 2 of the humeral neck 4 is able to engage the socket depression 1b of the humeral head 1a such that said head is capable of rotating along any circumference of the proximal ball end 2 of the humeral neck 4 and independent of the relative sizes of these components.

As more fully discussed below, the prosthesis is advantageously configured for mating of the socket depression 1b of the planar surface 1c of the humeral head 1a with the proximal ball end 2 of the humeral neck 4 by the surgeon who may relatively position the head 1a and neck 4 at a radial tilt angle that exactly duplicates the natural tilt angle of the patients humeral head. This is possible because the advantageous overhang 3 allows the head to be placed at an angle up to 90 degrees from the humeral neck without abutting the humeral neck itself. FIG. 3 illustrates this advantageous feature.

Pre-operative radiographic evaluation should include a complete shoulder series consisting of an anteroposterior view of the shoulder in neutral, internal, and external rotation; outlet view; and axillary lateral view. Anteroposterior views enable the surgeon to determine the relationship of the humeral component to the tuberosities and shaft, assess the tuberosities for the presence of a delayed union or malunion, and evaluate superior and inferior positioning of the humeral head relative to the glenoid. Evaluation in the views assists the surgeon in determining the patient's natural radial tilt angle that will be duplicated with the variable tilt angle shoulder prosthesis.

To insert the variable tilt angle shoulder prosthesis according to a preferred embodiment, the humeral medullary canal may be reamed or broached, by hand or using power tools or other instruments known to those skilled in the art, until minimal resistance is met. This is more of a sizing procedure than a reaming procedure. Most of the patients who undergo prosthetic replacement for osteoarthritis are also osteopenic, so care must be taken to avoid splitting the proximal humerus by overzealous reaming or broaching. The surgeon should preferably ream or broach only as much of the medullary canal as may allow the insertion the shaft of the prosthetic humerus.

After the canal is prepared, the humeral shaft 5 is inserted by methods well known to those of ordinary skill in the art. Once the shaft 5 and neck 4 are in place, the head is installed at a selected radial tilt angle depending the anatomy of the individual patient as determined by radiography and intraoperative appearance. When the correct radial tilt angle has been set, the variable angle taper lock is secured in place.

Following insertion and fixation, the operative field is closed by standard techniques. The patient will require some bed rest for day, followed by a gradual return in activity, and will need to avoid lifting items for some period of time.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A shoulder prosthesis having a variable tilt angle, comprising:
   a head component including a proximal portion configured to interface with a glenoid process and a distal surface including a socket depression defined therein;
   a humeral shaft;
   a humeral neck at the end of the shaft including a proximal ball end which overhangs from a circumference of the humeral neck and which is configured to couple with the socket depression of the head component as a ball-in-socket joint; and
   wherein said head component is adjustable, upon coupling with said humeral neck, to a selected tilt angle among a plurality of tilt angles relative to an elongate direction of said shaft to substantially match said prosthesis to a natural tilt angle of a humeral component of a patient.

2. A shoulder prosthesis according to claim 1, wherein said head component is configured to be mated with said proximal ball end of said humeral neck such as to be disposed at a selected set position among a plurality of positions lattitudinally relative to said proximal ball end for substantially matching said prosthesis to a natural tilt angle of a head component of a patient.

3. A shoulder prosthesis according to claim 2, wherein said head component is configured to be rotated, after being mated with said humeral neck, in a latitudinal direction relative to said proximal ball end of said neck to a set position for substantially matching said prosthesis to a natural tilt angle of the humeral head component of a patient.

4. A shoulder prosthesis according to claim 1, wherein said socket depression of the head component is hemispherical.

5. A shoulder prosthesis according to claim 1, wherein said distal surface of the humeral component is planar.

6. A shoulder prosthesis according to claim 1, wherein said proximal ball end of the humeral neck is hemispherical.

7. A shoulder prosthesis according to claim 1, wherein said proximal ball end has an overhang that extends from the circumference of the humeral neck.

8. A variable tilt angle shoulder prosthesis according to claim 1, further comprising a fin extending superiorly from an angled portion of the humeral neck.

9. A variable tilt angle prosthesis according to claim 1, wherein said humeral shaft and neck, and head component, comprise metal.

10. A variable tilt angle prosthesis according to claim 9, wherein said metal comprises cobalt chrome steel.

11. A variable tilt angle prosthesis according to claim 9, wherein said metal comprises titanium.

12. A variable tilt angle prosthesis according to claim 1, wherein said humeral shaft and neck, and head component, comprise plastic.

13. A variable tilt angle prosthesis according to claim 1, wherein said humeral shaft and neck, and head component, comprise polyethylene.

14. A variable tilt angle prosthesis according to claim 1, wherein said humeral shaft and neck are configured according to a selected tilt angle and length among a plurality of available tilt angles and lengths.

15. A variable tilt angle prosthesis according to claim 14, wherein said humeral shaft is configured to have a length that is only enough to secure the shaft in a humerus of a patient.

16. A method of replacing a humeral head of a patient with a variable tilt angle prosthesis, comprising the steps of:
(a) resecting a proximal end of a humerus of the patient to remove the head and expose a medullary canal of the humerus;
(b) inserting a stem of a prosthesis, said prosthesis including a humeral shaft, a humeral neck and a head component adapted to approximate a dimension of said humeral head of said patient, into the medullary canal of the resected humerus; said head component having a proximal portion configured to interface with a glenoid process and a distal surface including a socket depression defined therein; said humeral neck at the end of the shaft including a proximal ball end which overhangs from a circumference of the humeral neck and which is configured to couple with the socket depression of the head component as a ball-in-socket joint; and wherein said humeral head component is adjustable to a selected tilt angle among a plurality of tilt angles relative to an elongate direction of said shaft to substantially match said prosthesis to a natural tilt angle of the humeral head of the patient; and
(c) setting said head component, upon coupling with said humeral neck, to a selected tilt angle among a plurality of tilt angles relative to an elongate direction of said shaft to substantially match said prosthesis to a natural tilt angle of the humeral head of the patient.

17. A method of replacing a humeral head of a patient with a shoulder prosthesis according to claim 16, wherein said head component is set at a position among a plurality of positions lattitudinally relative to said proximal ball end of said humeral neck to substantially match a natural tilt angle of the humeral head of a the patient.

18. A method of replacing a humeral head of a patient with a shoulder prosthesis according to claim 17, and wherein said setting of said prosthesis is performed by the following steps:
(i) observing a first position for the socket depression of the head component at the apex of the proximal ball end of said humeral neck;
(ii) selecting a second position from among a plurality of points along a lattitude of the proximal ball end of the humeral neck located at about 30 degrees from the apex of said proximal ball end;
(iii) adjusting the lattitudinal position of the apex of the socket depression relative to the apex of the proximal ball end of the humeral neck along the longitude between the first and second position.

19. A method of replacing a humeral head of a patient with a shoulder prosthesis according to claim 18 wherein the setting said prosthesis head upon coupling with said humeral neck is performed by rotating said head component to a selected tilt angle among a plurality of tilt angles relative to an elongate direction of said shaft to substantially match said prosthesis to a natural tilt angle of the humeral head of a patient.

20. A method of replacing a humeral head of a patient with a variable tilt angle prosthesis according to claim 19, and wherein said setting of said prosthesis is performed by the following steps:
(i) observing a first position for the socket depression of the head component at the apex of the proximal ball end of said humeral neck;
(ii) selecting a second position from among a plurality of points along a lattitude of the proximal ball end of the humeral neck located at about 30 degrees from the apex of said hemispherical proximal dome;
(iii) rotating the lattitudinal position of the apex of the socket depression relative to the apex of the proximal ball end of the humeral neck along the longitude between the first and second position.

21. A method of replacing a humeral head of a patient with a variable tile angle prosthesis according to claim 18 further comprising the step of securing the head component at the patient's natural radial tilt angle.

* * * * *